United States Patent
Manion et al.

(10) Patent No.: US 9,717,455 B2
(45) Date of Patent: Aug. 1, 2017

(54) PORTABLE FLOW METER FOR LOW VOLUME APPLICATIONS

(71) Applicant: Empire Technology Development LLC, Wilmington, DE (US)

(72) Inventors: Michael Manion, Seattle, WA (US); Benjamin William Millar, Rosebery (AU); George Charles Peppou, Rosebery (AU)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 0 days.

(21) Appl. No.: 14/675,295

(22) Filed: Mar. 31, 2015

(65) Prior Publication Data
US 2016/0287164 A1    Oct. 6, 2016

(51) Int. Cl.
*F16K 99/00*    (2006.01)
*A61B 5/00*    (2006.01)
(Continued)

(52) U.S. Cl.
CPC .............. *A61B 5/4266* (2013.01); *A61B 5/01* (2013.01); *A61B 5/024* (2013.01); *A61B 5/1118* (2013.01);
(Continued)

(58) Field of Classification Search
CPC ............ Y10T 137/7761; A61B 5/4266; A61B 10/0064; F16K 37/005; F16K 31/0644;
(Continued)

(56) References Cited

U.S. PATENT DOCUMENTS 4,962,662 A * 10/1990 Berger ................... G01N 30/28
                                                73/23.42
5,050,604 A *  9/1991 Reshef ................. A61B 5/4266
                                                600/346
(Continued)

FOREIGN PATENT DOCUMENTS

CN    103054556 A       4/2013
JP    H07209056         8/1995
WO    2013179240 A1    12/2013

OTHER PUBLICATIONS

Form PCT/ISA/206 received for PCT/US2016/019305 dated Apr. 14, 2016.
(Continued)

*Primary Examiner* — Matthew W Jellett
(74) *Attorney, Agent, or Firm* — Dorsey & Whitney LLP

(57) ABSTRACT

An apparatus is disclosed that may include a substrate that may have a surface, a channel of a volume that may be defined, at least in part, by the substrate, wherein the channel may have a first end and a second end, a valve may be coupled to the channel at the first end, wherein the valve may be configured to allow a fluid to pass into the channel when the valve is open, and a continuity detector, which may be coupled to the channel at the second end, wherein the continuity detector may be activated when the fluid contacts the continuity detector, wherein the continuity detector may further be configured to provide a signal to close the valve and remove the fluid from the channel. A method for calculating a rate of flow of a fluid collected from a bodily surface into a body-worn device is disclosed.

17 Claims, 7 Drawing Sheets

(51) Int. Cl.
*A61B 5/01* (2006.01)
*A61B 5/024* (2006.01)
*A61B 5/11* (2006.01)
*F16K 31/06* (2006.01)
*G01F 15/00* (2006.01)
*G05D 7/06* (2006.01)
*F16K 37/00* (2006.01)
*G01F 25/00* (2006.01)
*G01F 3/02* (2006.01)

(52) U.S. Cl.
CPC ........ *F16K 31/0644* (2013.01); *F16K 37/005* (2013.01); *F16K 99/0048* (2013.01); *G01F 3/02* (2013.01); *G01F 15/005* (2013.01); *G01F 25/003* (2013.01); *G01F 25/0007* (2013.01); *G01F 25/0046* (2013.01); *G05D 7/0635* (2013.01); *F16K 2099/0094* (2013.01); *Y10T 137/7761* (2015.04)

(58) Field of Classification Search
CPC ........ F16K 99/0048; F16K 2099/0094; G05D 7/0635
USPC ............ 137/487.5; 600/307, 346, 362
See application file for complete search history.

(56) References Cited

U.S. PATENT DOCUMENTS

| | | | |
|---|---|---|---|
| 5,131,390 A | 7/1992 | Sakaguchi et al. | |
| 5,224,510 A * | 7/1993 | Pericles | F16K 31/004 137/341 |
| 5,417,235 A * | 5/1995 | Wise | B01J 19/0093 137/1 |
| 6,076,522 A | 6/2000 | Dwivedi et al. | |
| 6,095,175 A * | 8/2000 | Miller | F16K 31/004 137/15.18 |
| 6,206,022 B1 * | 3/2001 | Tsai | G05D 7/0694 137/15.18 |
| 6,269,265 B1 | 7/2001 | Anderson | |
| 6,349,740 B1 * | 2/2002 | Cho | A61M 5/14276 137/487.5 |
| 6,539,968 B1 * | 4/2003 | White | G05D 7/0635 137/10 |
| 7,124,773 B2 * | 10/2006 | Midtgard | F16K 31/004 137/375 |
| 7,666,687 B2 * | 2/2010 | Webster | B01L 3/50273 422/503 |
| 7,918,238 B2 * | 4/2011 | Tanaka | G01F 1/6847 137/10 |
| 8,650,946 B1 | 2/2014 | Feller | |
| 8,789,556 B2 * | 7/2014 | Yasuda | G01F 25/0053 118/715 |
| 2004/0107996 A1 * | 6/2004 | Crocker | G05D 7/0694 137/487.5 |
| 2004/0202548 A1 | 10/2004 | Dai et al. | |
| 2005/0160833 A1 | 7/2005 | Gerhardt et al. | |
| 2005/0287043 A1 | 12/2005 | Stromereder et al. | |
| 2007/0089789 A1 * | 4/2007 | Mudd | G01F 1/86 137/487.5 |
| 2009/0054746 A1 | 2/2009 | Cho | |
| 2009/0105605 A1 | 4/2009 | Abreu | |
| 2010/0063372 A1 | 3/2010 | Potts et al. | |
| 2010/0132485 A1 | 6/2010 | Erez et al. | |
| 2011/0111516 A1 | 5/2011 | Lee et al. | |
| 2012/0090703 A1 * | 4/2012 | Li | F16H 61/0251 137/487.5 |
| 2012/0150072 A1 | 6/2012 | Revol-Cavalier et al. | |
| 2013/0129580 A1 | 5/2013 | Flavin et al. | |
| 2013/0253872 A1 | 9/2013 | Curtis et al. | |
| 2013/0303967 A1 | 11/2013 | Utz et al. | |
| 2014/0066867 A1 | 3/2014 | Locke et al. | |
| 2015/0316172 A1 * | 11/2015 | Bustgens | F16K 99/0048 137/487.5 |

OTHER PUBLICATIONS

"Body surface area", accessed at http://web.archive.org/web/20140809191033/http://en.wikipedia.org/wiki/Body_surface_area, last modified on Aug. 3, 2014 pp. 5.
"Perspiration", accessed at http://web.archive.org/web/20140626125314/http://en.wikipedia.org/wiki/Perspiration, last modified on May 14, 2014, pp. 7.
Bois, D et al., "A formula to estimate the approximate surface area if height and weight be known", Arch Int Med 1916 17, 863-871.
Coyle, S et al., "Textile sensors to measure sweat pH and sweat-rate", In: Pervasive Health 2009, London, UK. ISBN 978-963-9799-42-4, Apr. 13, 2009, 1-6.
Feng, Y et al., "Passive valves based on hydrophobic microfluidics. Sensors and Actuators", 108, http://www.sciencedirect.com/science/article/pii/S0924424703003637, Nov. 15, 2003, 138-143.
Klinker, L E., "Skin-Based Sweat Monitoring Using Radio Frequency Identification Sensors", 2012, 1-97.
Kono, T et al., "Wearable Sized Sudorometer and Sweat Measurement", Sep. 6, 2013, 1-1.
Kraning, KK et al., "Measurement of sweating rate with capacitance sensors", Annals of Biomedical Engineering 11(2), http://link.springer.com/article/10.1007/BF02367496, 1983, 131-146.
Leng, H et al., Design and fabrication of a MEMS/NANO-skin system for human physiological response measurement, SPIE | Proceeding, Oct. 21, 2013, 1-1.
Maughan, R J., "Impact of mild dehydration on wellness and on exercise performance", Eur. J. Clin. Nutr., vol. 57, No. 2, 2003, S19-S23.
McClure, J A. et al., "A Sweat Sensor for Qualitative Measurements", Nov. 15, 1971, 1-24.
Pw, L et al., "Feasibility of sweat collection by whole body washdown in moderate to high humidity environments", International journal of Sports Medicine. 6, http://www.ncbi.nlm.nih.gov/pubmed/3988414, Feb. 6, 1985, 41-43.
Saco, J J., "The Average Body Surface Area of Adult Cancer Patients in the UK: A Multicentre Retrospective Study", PLoS One 5 (1), Jan. 28, 2010, 1-6.
Salvo, P et al., "A Wearable Sensor for Measuring Sweat Rate", IEEE Sensors Journal, vol. 10, 2010, 1-2.
Smith, C J. et al., "Body Mapping of Sweating Patterns in Athletes", Med Sci Sports Exerc. 4(12), 2350-2361.
Yokata, M et al., "Transient Sweat Rate Calculation from Humidity", 2006, 1-10.
International Search Report and Written Opinion received for PCT/US2016/019305 dated Jun. 30, 2016.
International search report and written opinion for International Application No. PCT/US2016/037302 mailed on Sep. 27, 2016, pages 6.

* cited by examiner

PORTABLE FLOW METER FOR LOW VOLUME APPLICATIONS

BACKGROUND

Flow meters calculate flow rates, which is the volume of fluid that passes through a measurement point during a period of time. For example, utility companies may use flow meters to determine how much water a household used during a month to calculate monthly usage fees.

Measuring the flow rate of low volumes of fluids with low flow rates may be more difficult than measuring the flow rate of large volumes. Surface tension of the fluid and/or surfaces of the flow meter may affect the observed flow rate of the flow meter. For example, a plant may produce secretions on its stem. The stem may have a small observable area, and the secretions may occur over hours or days. Determining a secretion rate of the plant with traditional flow meters may not be feasible.

SUMMARY

Techniques are generally described that include apparatuses, methods, and systems. An example apparatus may include a substrate which may have a surface, a channel which may have a volume defined, at least in part, by the substrate, wherein the channel may have a first end and a second end, a valve coupled to the channel at the first end, wherein the valve may be configured to allow a fluid to pass into the channel when the valve is open, and a continuity detector coupled to the channel at the second end, wherein the continuity detector may be activated when the fluid contacts the continuity detector, wherein the continuity detector may be further configured to provide a signal to close the valve and remove the fluid from the channel.

An example method may include collecting a fluid from a bodily surface into a body-worn device, filling a channel of the body-worn device with the fluid, measuring, using the body-worn device, a time it takes to fill the channel with the fluid, removing the fluid from the channel, and calculating, using the body-worn device, a rate of flow of the fluid based, at least in part, on the time it takes to fill the channel with the fluid.

An example system may include a sensor that may be configured to monitor a flow of a fluid from a bodily surface area through a channel of a volume, a first processor that may be configured to receive signals from the sensor and calculate a flow rate of the fluid, and a computing device, including a second processor that may be configured to receive the flow rate of the fluid from the first processor and combine the flow rate of the fluid with additional data to calculate a health status of a user.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1:
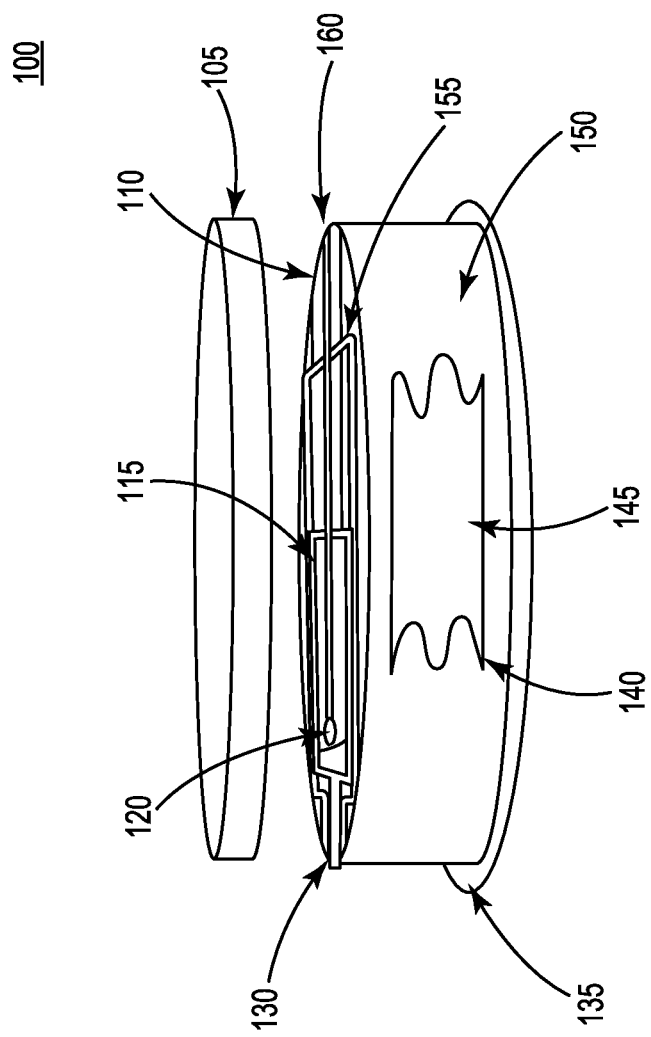
FIG. 1 is a schematic illustration of an example flow meter.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

This disclosure is drawn, inter alia, to methods, systems, products, devices, and/or apparatus generally related to an apparatus that may include a substrate that may have a surface, a channel of a volume that may be defined, at least in part, by the substrate, wherein the channel may have a first end and a second end, a valve may be coupled to the channel at the first end, wherein the valve may be configured to allow a fluid to pass into the channel when the valve is open, and a continuity detector, which may be coupled to the channel at the second end, wherein the continuity detector may be activated when the fluid contacts the continuity detector, wherein the continuity detector may further be configured to provide a signal to close the valve and remove the fluid from the channel.

FIG. 1 is a schematic illustration an example flow meter 100 arranged in accordance with at least some embodiments described herein. The flow meter 100 includes a sensor 160 that may be enclosed in a substrate 150. The substrate 150 may include an upper layer 105 disposed over the sensor 160. FIG. 1 shows the upper layer 105 removed from the substrate 150 for clarity. The sensor 160 may include a channel 110 with electrodes 115 coupled to the channel 110, an opening 120 in the channel, an I/O port 130, and a continuity detector 155 spanning the channel 110. The substrate 150 may enclose an absorbent material 145, which may be seen through cutaway 140 in FIG. 1. The opening 120 may couple the channel 110 to the absorbent material 145. A seal 135 may be coupled to a lower surface of the substrate 150. The various components described in FIG. 1 are merely examples, and other variations, including eliminating components, combining components, and substituting components are all contemplated.

In some embodiments, the upper layer 105 of the substrate 150 is a removable lid placed over the sensor 160. In some embodiments, the upper layer 105 is permanently coupled to the substrate 150. In some embodiments, the upper layer 105 is the same material as the substrate 150. In some embodiments, the upper layer 105 and the substrate 150 are implemented using different materials. The upper layer 105 and substrate 150 may be implemented using a polymer, glass, silicone, and/or metal. Other materials may also be used.

In some embodiments, the sensor 160 may include a piezoelectric material that at least partially defines the channel 110. In some examples, the substrate 150 at least partially defines the channel 110 and the substrate 150 is implemented using a piezoelectric material. In some examples, the piezoelectric material may be included in the substrate 150. The piezoelectric material may be activated by the electrodes 115. The application of an electrical charge through the electrodes 115 may cause the piezoelectric material to contract and cause the channel 110 and opening 120 to open and close. In some embodiments, the piezoelectric material may be replaced by an electromagnetic actuator that may be used to open and close the channel 110 and opening 120.

In some embodiments, the electrodes 115 may be activated by a signal received from the continuity detector 155. The electrodes 115 may deactivate when the signal is no longer received from the continuity detector 155. In some embodiments, the electrodes may be activated by a control signal received from the I/O port 130. In some embodiments, the continuity detector 155 may send signals to the I/O port 130. In some embodiments, the I/O port 130 may couple the flow meter 100 to a processor and/or other computing device.

In some embodiments, the seal 135 may extend around a perimeter of the lower surface of the substrate 150. The seal 135 may be implemented using rubber, silicone, and/or another non-porous elastomer. In some embodiments, the seal 135 may allow the flow meter 100 to adhere to a surface. In some embodiments, the flow meter 100 is held in place against a surface by a strap (not shown). In some embodiments, the seal 135 may be substantially impermeable and may prevent fluids from entering or exiting the flow meter 100 from the lower surface of the substrate 150. In some embodiments, the seal 135 may define an area of a surface over which a flow rate is measured. In some embodiments, the area may be between 0.1 and 5 square centimeters. Other areas may also be possible.

In some embodiments, the substrate 150 has an interior portion that may at least partially enclose the absorbent material 145. The absorbent material 145 may extend from the lower surface of the substrate 150 to the opening 120 of the channel 110. In some embodiments, the absorbent material 145 may conduct fluids proximate to the lower surface of the substrate 150 to the opening 120.

In operation, the flow meter 100 may be coupled to a surface over which a fluid flow rate is to be measured. Examples include, but are not limited to, human skin, a leaf, and/or a membrane. The lower surface of the flow meter 100 may be placed in contact with the surface. The seal 135 may adhere to the surface and/or a strap (not shown) may be applied to the flow meter 100 to maintain contact with the surface. The seal 135 may enclose an area of the surface over which the flow meter 100 is placed. The seal 135 may prevent fluid emitted from the surface area under the flow meter 100 from flowing out under the lower surface of the flow meter 100. The seal 135 may further prevent fluid emitted from the surface outside the area under the flow meter 100 from entering the flow meter 100 through the lower surface. This may allow fluid flow to be measured from a fixed area of the surface.

Fluid emitted by the surface area under the flow meter 100 may contact the absorbent material 145. The absorbent material 145 may conduct the fluid from the surface to the opening 120. The fluid may flow through the opening 120 into the channel 110 of the sensor 160. As more fluid is emitted from the surface area under the flow meter 100, more fluid may be conducted by the absorbent material 145 to the channel 110. The fluid may fill the channel 110 to where the fluid contacts the continuity detector 155. The continuity detector 155 may send a signal to the electrodes 115 and/or the I/O port 130 when the fluid contacts the continuity detector 155. In response to a signal from the continuity detector 155 and/or I/O port 130, the electrodes 115 may apply a charge to a piezoelectric material of the channel 110. The charge may cause the piezoelectric material to activate.

The piezoelectric material may close the opening 120, which may prevent fluid in the channel 110 from flowing back into the absorbent material 145. The piezoelectric material may also close the body of the channel 110 such that fluid is forced out of the end of the channel 110 proximate to the continuity detector 155. In some embodiments, actively removing the fluid from the channel 110 may prevent surface tension and/or other interactions between the fluid and the channel 110 from interfering with measuring a flow rate of the fluid emitted from the surface.

In some embodiments, the expelled fluid may drip down the outer surface of the substrate 150 of the flow meter 100. The expelled fluid may be prevented from reentering the flow meter 100 by seal 135. Optionally, in some embodiments, the expelled fluid may be collected in a receptacle (not shown) coupled to the flow meter 100. The receptacle may retain the fluid for future analysis. Once the fluid has been expelled from the flow meter 100, the electrodes 115 may stop applying a charge to the piezoelectric material, which may then return to a rest state. In the rest state, the channel 110 and opening 120 are opened, and fluid emitted from the surface may continue to enter the channel 110. The fluid may again be expelled when it contacts the continuity detector 155.

In some embodiments, the flow rate of the fluid emitted from the surface may be calculated based, at least in part, on the number of times the fluid is expelled from the channel during a period of time. In some embodiments, a clock (not shown) may be used to measure the time it takes to fill the channel 110. In some embodiments, the clock may be coupled to the flow meter 100 through I/O port 130. In some embodiments, the clock is included in a computing device coupled to the I/O port 130. The clock may receive a signal from the continuity detector 155 via the I/O port 130, which may signal that the channel 110 has been filled with the fluid. In some embodiments, the clock may be configured to measure a time period and reset each time the continuity detector is activated. In some embodiments, the clock may be coupled to a processor. In some embodiments, the clock may be integrated with the processor. In some embodiments, the processor is included in the computing device. The processor may be configured to receive the time period from the clock and calculate a rate of flow of the fluid through the channel 110, based at least in part on the time period from the clock. In some embodiments, the flow rate may further be based at least in part on the volume of the channel 110.

Figure 2:
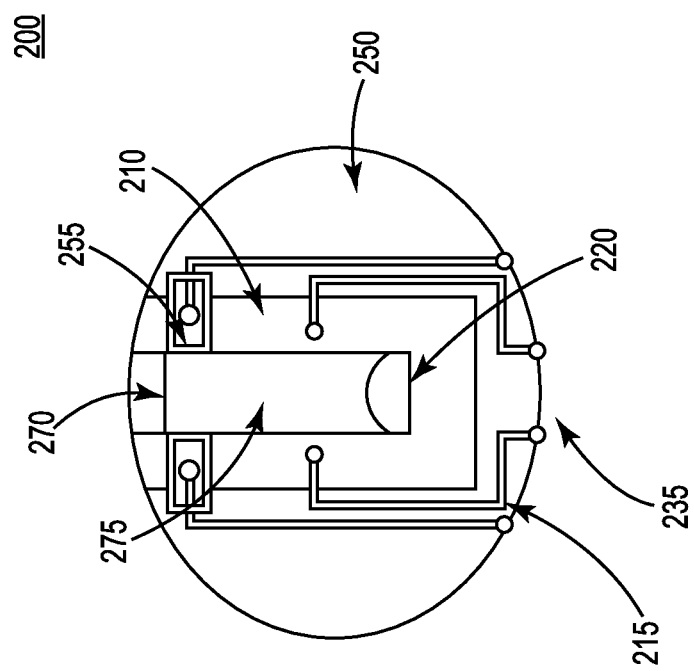
FIG. 2 is a schematic illustration of an example sensor.

FIG. 2 is a schematic illustration of an example sensor 200 arranged in accordance with at least some embodiments described herein. In some embodiments, sensor 200 may be used to implement the sensor 160 illustrated in FIG. 1. In some embodiments, the sensor 200 may be included on a substrate 250. In some embodiments, the substrate 250 may be implemented with the substrate 150 illustrated in FIG. 1. FIG. 2 shows a piezoelectric material 210 that at least partially defines a channel 275. A continuity detector 255 may be coupled to the piezoelectric material 210. Electrodes 215 may also be coupled to the piezoelectric material 210. A valve 220 may be located at one end of the channel 275 opposite the continuity detector 255. A stop valve 270 may be included in the channel 275 near the continuity detector 255 at an end opposite the valve 220. The electrodes 215 and/or continuity detector 255 may be coupled to an I/O port 235. In some embodiments, the sensor 200 may be coupled to a computing device via the I/O port 235. The various components described in FIG. 2 are merely examples, and other variations, including eliminating components, combining components, and substituting components are all contemplated.

In some embodiments, the sensor 200 may be configured such that a fluid may enter the channel 275 via the valve 220 and flow through the channel 275 toward the continuity detector 255. In some embodiments, fluid may be prevented from entering the channel 275 via the stop valve 270. In some embodiments, fluid may be prevented from exiting the channel 275 via the stop valve 270. In some embodiments, fluid may exit the channel 275 via the stop valve 270 when the piezoelectric material 210 is activated. In some embodiments, the channel 275 may contract and expel the fluid from the channel 275 when the piezoelectric material 210 is activated. In some embodiments, the piezoelectric material 210 is activated by the electrodes 215. The electrodes 215 may activate the piezoelectric material 210 when it receives a signal from the continuity detector 255. The continuity detector 255 may send a signal to activate the piezoelectric material 210 when fluid in the channel 275 contacts the continuity detector 255.

In some embodiments, the channel 275 may have a volume defined at least in part by the piezoelectric material 210. In some embodiments, the channel 275 may have a volume defined at least in part by the substrate 250. In some embodiments, both the piezoelectric material 210 and the substrate 250 may at least partially define the volume. In some embodiments, the volume of the channel 275 may be about 10 nanoliters to about 100 nanoliters. In some embodiments, the volume of the channel 275 may be about 100 nanoliters to about 1,000 nanoliters. In some embodiments, the volume of the channel 275 may be about 1 microliter to about 10 microliters. Other volumes may also be possible.

In some embodiments, the fluid may only pass in one direction through the channel 275. In some embodiments, the valve 220 is a one-way valve that only allows fluids to enter the channel 275. In some embodiments, the valve 220 is an opening in the channel 275. In some embodiments, the stop valve 270 is a hydrophobic material. In some examples, the stop valve 270 is made of siloxane. In some embodiments, the stop valve 270 is omitted, and the end of the channel 275 proximate the continuity detector 255 is open. In some embodiments, the valve 220 is configured to close before the stop valve 270 is opened when the piezoelectric material 210 is activated.

In some embodiments, additional sensors (not shown) may be included in the channel 275 for additional data acquisition. In some embodiments, the continuity detector 255 may collect additional data. Additional data may include detecting and/or quantifying analytes of interest in the fluid, temperature of the fluid, pH level of the fluid, and/or other fluid properties. Examples of analytes of interest may include, but are not limited to, lactate, potassium, sodium, glucose, proteins, and/or other chemicals. In some embodiments, the sensors are electrochemical sensors. In some embodiments, the sensors are optical sensors. In some embodiments, multiple sensor types may be included in the channel 275.

In some embodiments, the electrodes 215, continuity detector 255, and/or additional sensors may be coupled to the I/O port 235. The I/O port 235 may receive and/or send signals to the electrodes 215, continuity detector 255, and/or additional sensors. In some embodiments, the I/O port 235 may receive data signals from the continuity detector 255 and/or additional sensors. The I/O port 235 may provide the data signals to a computing device configured to store and/or process the data from the data signals. The I/O port 235 may provide the data signals via a wired connection, a wireless connection, or both. The computing device may be configured to analyze the data to calculate a flow rate of the fluid. The computing device may be configured to analyze the data and/or additional data to determine a health status of a user. The computing device may send control signals to the sensor 200 via the I/O port 235 in some embodiments. For example, the computing device may send a control signal to the electrodes 215 to apply a charge to the piezoelectric material 210. In some embodiments, additional control signals may be sent by the computing device.

Figure 3:
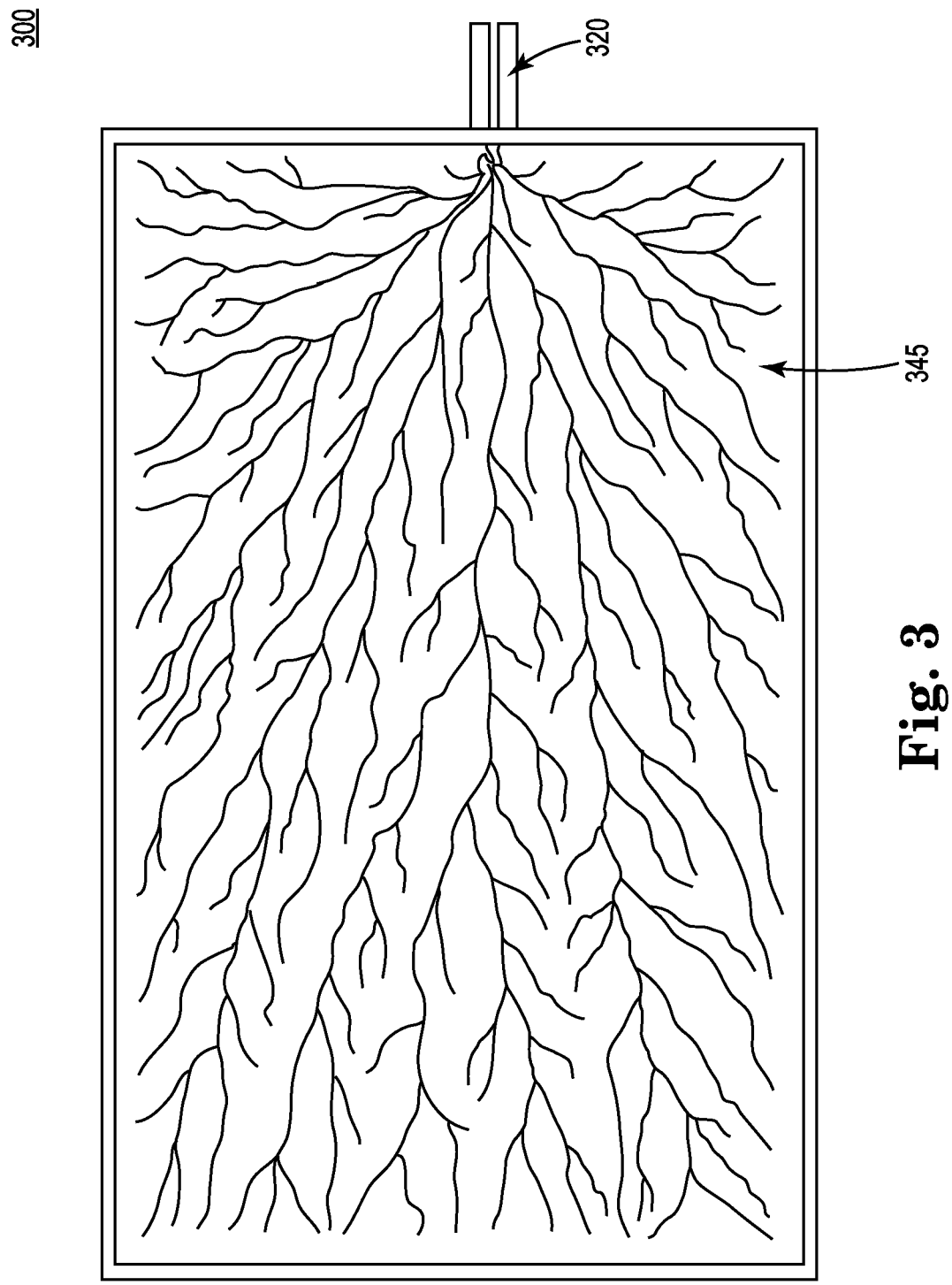
FIG. 3 is a schematic illustration of an example absorbent material.

FIG. 3 is a schematic illustration of an example absorbent material 300. The absorbent material 300 may be used as the absorbent material 145 in FIG. 1. FIG. 3 shows a conduit system 345 coupled to an opening 320. The various components described in FIG. 3 are merely examples, and other variations, including eliminating components, combining components, and substituting components are all contemplated.

In some embodiments, the absorbent material 300 may be implemented utilizing a sponge or a hydrogel. In some embodiments, the absorbent material 300 is cotton. In some embodiments, other absorbent materials or combination of absorbent materials are utilized. In some embodiments, as illustrated in FIG. 3, the absorbent material 300 may be a printed and/or etched branched conduit system 345 of converging capillaries. The conduit system 345 may draw fluid from a surface and direct the fluid toward the opening 320. The fluid may be drawn by capillary action and/or some other force. In some embodiments, the conduit system 345 is etched and/or printed in a semi-rigid polymer or hardened elastomer.

In some embodiments, the absorbent material 300 is saturated with a fluid prior to operation of a flow meter (not shown in FIG. 3). Pre-saturating the absorbent material 300 may reduce or eliminate lag and/or priming time of the flow meter. In some embodiments, at the saturation point of the absorbent material 300, any fluid added to absorbent material 300 may displace an equivalent amount of fluid at the opening 320. In some embodiments, the priming fluid used to pre-saturate the absorbent material 300 is distilled water. In some embodiments, the priming fluid is saline.

In some embodiments, the opening 320 is at the top of the absorbent material 300. In some embodiments, the opening 320 is on a side of the absorbent material 300. In some embodiments, the opening 320 may be an opening in a substrate, such as the substrate 150 in FIG. 1. In some embodiments, the absorbent material 300 is cone-shaped. In some embodiments, the absorbent material 300 is cylinder shaped. Other shapes may be possible. In some embodiments, the absorbent material 300 may be at least partially enclosed in a substrate. In some embodiments, the absorbent material 300 may be removably coupled to the substrate, such that the absorbent material 300 may be disposable and be replaced by a new absorbent material after one or more uses. In some embodiments, the absorbent material 300 may be adjacent to a surface from which fluid flow is to be measured. The absorbent material 300 may conduct a fluid from the surface to the opening 320. The fluid may then pass through the opening 320. In some embodiments, the opening 320 may lead to and may be in fluid communication with a channel in a flow meter such as the channel 275 in FIG. 2.

Figure 4:
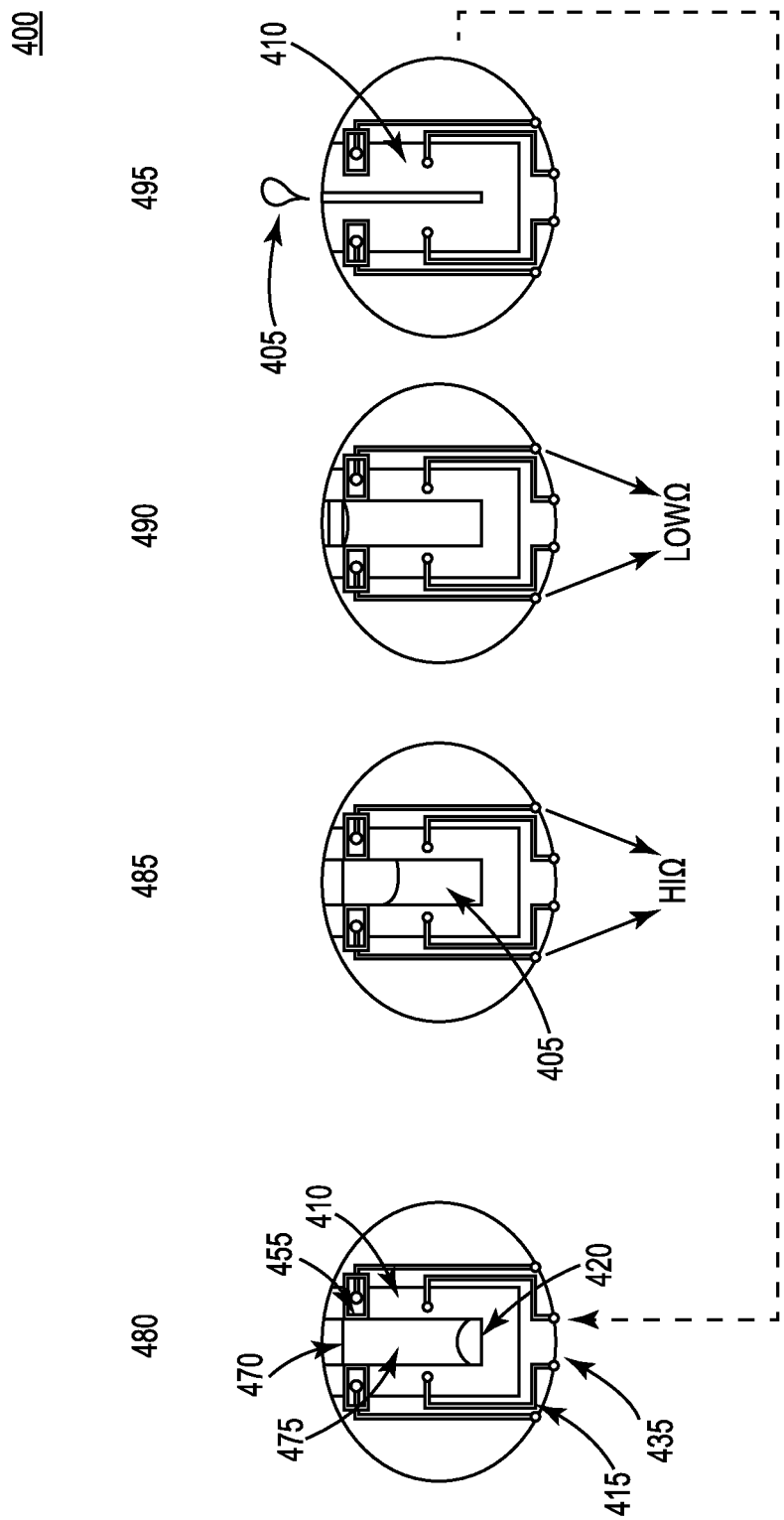
FIG. 4 is a schematic illustration of an example sensor in example stages of operation.

FIG. 4 is a schematic illustration of an example sensor 400 in example stages of operation. The sensor 400 may be similar to the sensor 200 in FIG. 2. In some embodiments, the sensor 160 in FIG. 1 may be implemented using sensor 400. FIG. 4 shows a piezoelectric material 410 that at least partially defines a channel 475. A continuity detector 455 may be coupled to the piezoelectric material 410. Electrodes 415 may also be coupled to the piezoelectric material 410. A valve 420 may be defined at one end of the channel 475 opposite the continuity detector 455. A stop valve 470 may be included in the channel 475 near the continuity detector 455 at an end opposite the valve 420. A fluid 405 may enter the channel 475 via valve 420. The various components described in FIG. 4 are merely examples, and other variations, including eliminating components, combining components, and substituting components are all contemplated.

In some embodiments, the sensor 400 may begin in an empty-rest state 480. In state 480, little or no fluid 405 is present in the channel 475. In this state 480, the electrodes 415 are not active, and the electrodes 415 do not provide a charge to the piezoelectric material 410. The piezoelectric material 410 may be in a rest state when no charge is applied by the electrodes 415. When the piezoelectric material 410 is in a rest state, the valve 420 may allow fluid 405 to enter the channel 475, and the channel 475 may define a fixed volume. In some embodiments, the continuity detector 455 may detect a high resistance across the channel 475 in state 480. In some embodiments, the continuity detector 455 may be an open circuit in state 480.

In some embodiments, as fluid 405 begins to enter the channel 475, the sensor 400 may transition to state 485. The components may have similar positions and properties as in state 480. Once fluid 405 fills the channel 475 to the location where the continuity detector 455 is located, the sensor 400 enters state 490. In some embodiments, the continuity detector 455 may detect a low resistance across the channel 475 in state 490. In some embodiments, the fluid 405 may conduct a current across the channel 475 at the continuity detector 455. In some embodiments, the fluid 405 may close a circuit of the continuity detector 455. In response, in some embodiments, the continuity detector 455 may send a signal to a processor (not shown) via I/O port 435 and/or the electrodes 415. In some embodiments, the electrodes 415 receive a signal from the processor via I/O port 435. The processor may be coupled to the sensor 400 via I/O port 435. In some embodiments, the processor may be included in a computing device.

In some embodiments, once the electrodes 415 receive a signal, the sensor 400 may transition to state 495. In some embodiments, the signal received by the electrodes 415 may be an activation signal. In response the activation signal, the electrodes 415 may apply an electrical charge to the piezoelectric material 410. The piezoelectric material 410 may be activated in response to the electrical charge from the electrodes. In some embodiments, the piezoelectric material 410 may close the valve 420 and close the channel 475, expelling the fluid 405 from the channel 475 via the stop valve 470. Once the fluid 405 has been removed, the sensor 400 may return to state 480. In some embodiments, the sensor 400 may cycle through the states until fluid 405 no longer fills the channel 475. In some embodiments, the sensor 400 may act as a one-way pump of a known volume of the fluid 405.

In some embodiments, the continuity detector 455 may be coupled to a clock (not shown). The clock may be coupled to or included in a processor (not shown). The clock may count until it receives a signal from the continuity detector 455. In some embodiments, the clock may receive a signal from the continuity detector at state 490. When the clock receives the signal from the continuity detector 455, it may pass the count and/or other measure of time to a processor and/or a memory. In some embodiments, the clock may also reset when it receives the signal from the continuity detector 455 and begin counting again when the sensor 400 returns to state 480.

In some embodiments, a flow rate may be calculated based, at least in part, on the time the fluid 405 took to fill the channel 475. If the volume of the channel 475 is fixed and the time the fluid 405 took to fill the channel 475 is measured, the flow rate may be calculated in terms of volume/time in some embodiments. If an area over which the fluid 405 was collected is fixed, the flow rate may be calculated in terms of volume/time/area. In some embodiments, the clock, processor, and/or memory may be coupled to the flow meter via an I/O port such as I/O port 130 in FIG. 1. In some embodiments, the clock, processor, and/or memory may be included in the flow meter. In some embodiments, the flow meter may communicate wirelessly with the clock, processor, and/or memory, which may be located on one or more separate devices. Separate devices may include, but are not limited to a personal computer, a watch, a smart phone, and/or laptop.

In some embodiments, the flow meter shown in FIG. 1 may include the sensor 400 shown in FIG. 4. The flow meter may be coupled to a surface to measure the flow rate of a fluid from the surface. In some embodiments, a flow meter according to at least one embodiment may be coupled to a bodily surface. The flow meter may be used to calculate a rate of fluid flow on the bodily surface. For example, the rate of perspiration (e.g. sweat) on a subject's skin may be monitored with the flow meter. Monitoring the perspiration of a subject may provide information about the subject's exertion and/or hydration status. The previous example is for explanatory purposes only. It should not be interpreted as limiting the scope of the disclosure.

In some embodiments, the flow meter may further include or be coupled to additional sensors. For example, a heart rate monitor, exercise intensity, thermometer, oxygen sensor, and/or glucose monitor may be coupled to the flow meter. Data from the additional sensors may also be coupled to a processor and/or other computing device. The processor and/or computing device may use data from one or more of the sensors to calculate a health status of a user.

Figure 5:
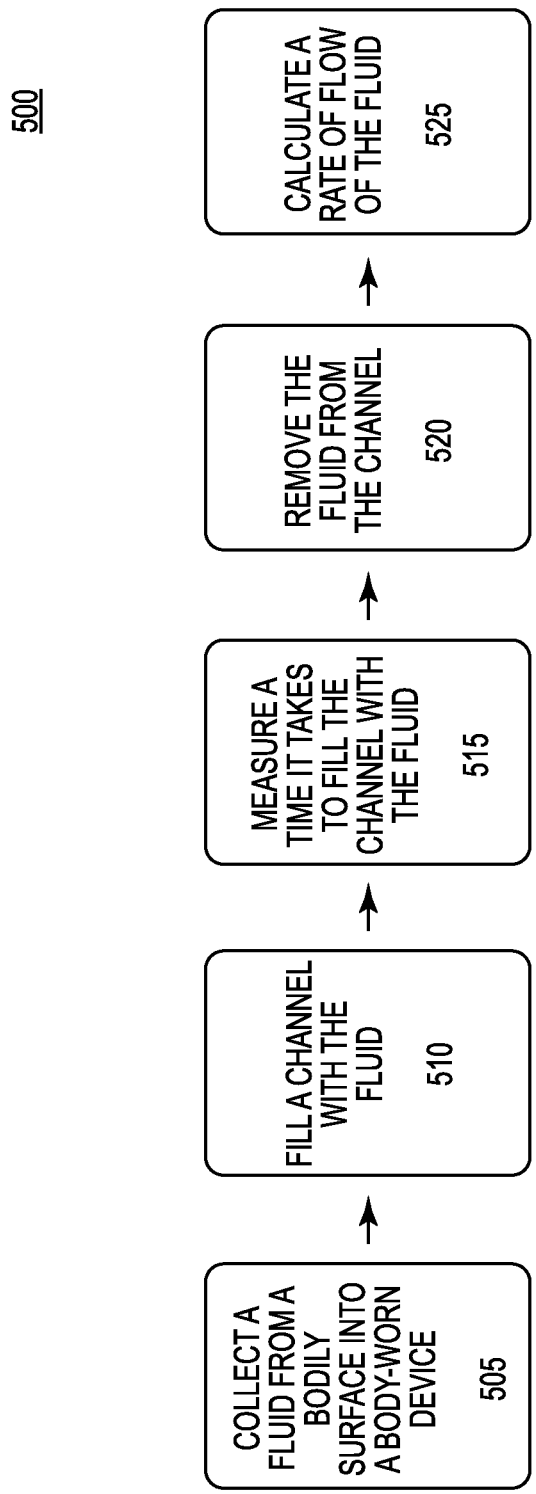
FIG. 5 is a flow chart of an example method.

FIG. 5 is a flow chart of an example method 500. An example method may include one or more operations, functions or actions as illustrated by one or more of blocks 505, 510, 515, 520, and/or 525. The one or more of the operations described in the blocks 505 through 525 may be performed in response to execution (such as by one or more processors described herein) of computer-executable instructions stored in a computer-readable medium, such as a computer-readable medium of a computing device or some other controller similarly configured.

An example process may begin with block 505, which recites "Collect a fluid from a bodily surface into a body-worn device." Block 505 may be followed by block 510, which recites "Fill a channel with the fluid." Block 510 may be followed by block 515, which recites, "Measure a time it takes to fill the channel with the fluid." Block 515 may be followed by block 520, which recites, "Remove the fluid from the channel." Block 520 may be followed by block 525, which recites, "Calculate a rate of flow of the fluid."

The blocks included in the described example methods are for illustration purposes. In some embodiments, the blocks may be performed in a different order. In some other embodiments, various blocks may be eliminated. In still other embodiments, various blocks may be divided into additional blocks, supplemented with other blocks, or combined together into fewer blocks. Other variations of these specific blocks are contemplated, including changes in the order of the blocks, changes in the content of the blocks being split or combined into other blocks, etc. In some examples, block 525 "Calculate a rate of flow of the fluid" may be performed before block 520 "Remove the fluid from the channel."

Block 505 recites, "Collect a fluid from a bodily surface into a body-worn device." A body-worn device may be a flow meter. In some embodiments, the body-worn device may be the flow meter 100 as illustrated in FIG. 1. A bodily surface may be human skin in some embodiments. In some embodiments, the fluid may be perspiration. The flow meter may be coupled to the bodily surface by a seal, such as seal 135 in FIG. 1. In some embodiments, the flow meter may be coupled to the bodily surface by a strap. In some embodiments, an absorbent material included in the flow meter collects the fluid from the bodily surface and conducts it to a sensor in the flow meter, such as sensor 400 in FIG. 4.

Block 510 recites, "Fill a channel with the fluid." The channel may be included in the body-worn device. In some embodiments, the fluid collected by the absorbent material enters the channel through a valve and/or opening at one end of the channel. In some embodiments, the fluid may only flow in one direction through the channel.

Block 515 recites, "Measure a time it takes to fill the channel with the fluid." In some embodiments, a timer and/or clock measures the time from when the collection of the fluid begins until the channel is full. In some embodiments, a continuity detector, such as continuity detector 455 in FIG. 4, detects when the channel is full. The continuity detector may send a signal to the clock and/or timer that indicates the channel has been filled by the fluid. The clock and/or timer may transmit the time measured to fill the channel to a processor, a database, a memory, and/or another destination. In some embodiments, the clock and/or timer may begin measuring time until another signal is received from the continuity detector.

Block 520 recites, "Remove the fluid from the channel." Once the channel has been filed by the fluid, the channel is emptied. In some embodiments, the channel is emptied by applying an electric charge to a piezoelectric material that at least partially defines the channel. The piezoelectric material may close the channel and cause the fluid to be expelled from the channel when the electric charge is applied. In some embodiments, the piezoelectric material may be omitted, and an electromagnetic actuator may be used to close the channel and expel the fluid.

Block 525 recites, "Calculate a rate of flow of the fluid." A processor may receive the time measurement from the clock and/or timer in some embodiments. In some embodiments, the processor may calculate a relative fluid flow rate (e.g. channel fills/minute). In some embodiments, the volume of the channel may be known, and the processor may calculate an absolute fluid flow rate (e.g. nanoliters/minute). In some embodiments, the processor may calculate a relative fluid flow rate per a unit area (e.g. channel fills/minute/device area). In some embodiments, the area of a bodily surface may be known. In some embodiments, channel volume and area over which fluid was collected may be known, and the processor may calculate an absolute fluid flow rate per area (e.g. nanoliters/minute/centimeters squared). In some embodiments, the fluid may include sweat, and a rate of perspiration of a user may be calculated based, at least in part, on the rate of flow of the fluid.

Figure 6:
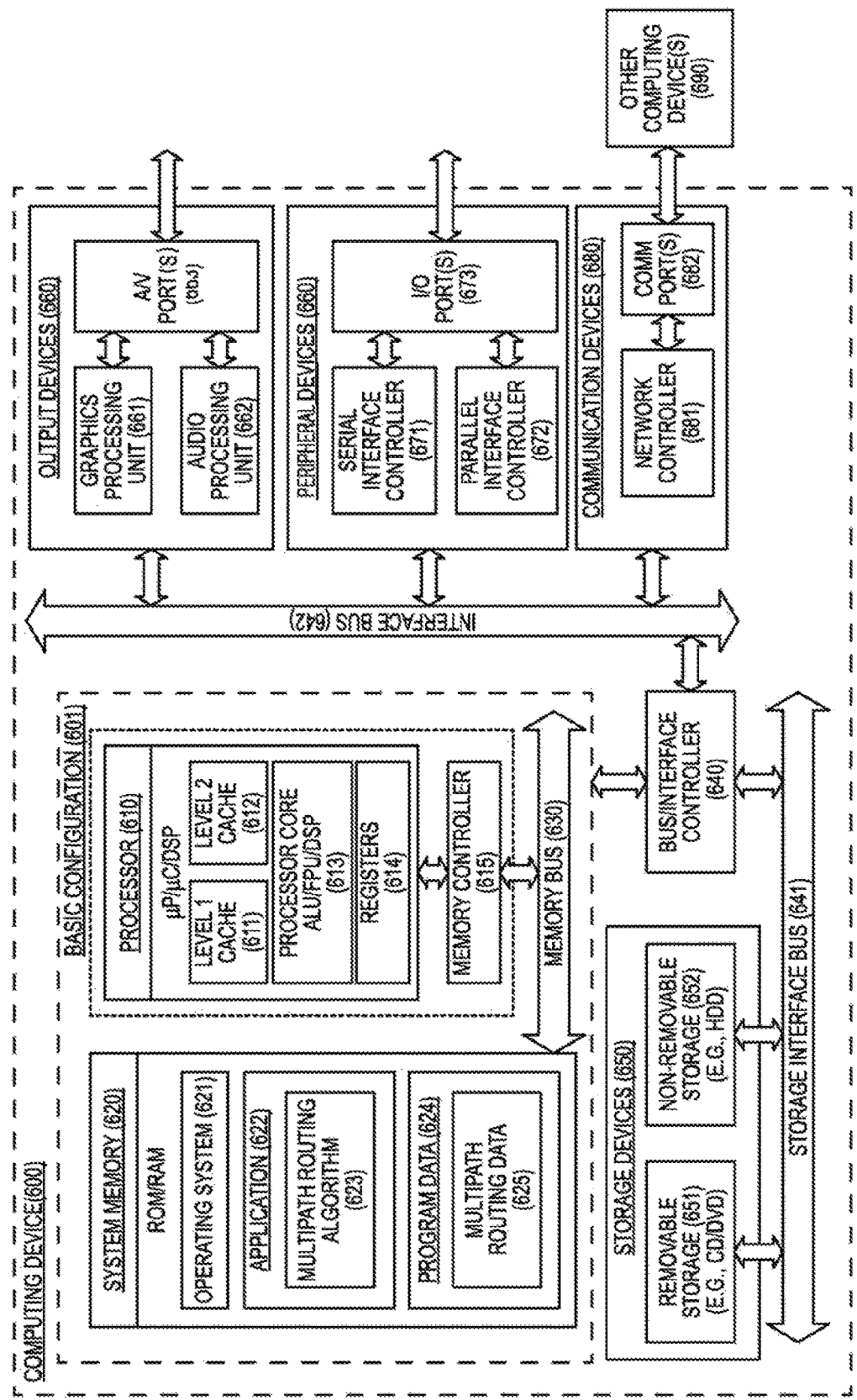
FIG. 6 is a block diagram illustrating an example computing device that is arranged for monitoring a flow rate.

FIG. 6 is a block diagram illustrating an example computing device 600 that is arranged for operating a flow meter and/or calculating a flow rate in accordance with the present disclosure. In some embodiments, the computing device 600 may be arranged to receive signals from a sensor configured to monitor a flow of a fluid from a bodily surface area through a channel of a volume and calculate a flow rate of the fluid and/or receive the flow rate of the fluid and combine the flow rate of the fluid with additional data to calculate a health status of a user. For example, the sensor from which the computing device 600 receives signals may be configured as any of the sensor examples disclosed herein such as the sensor 200 or 400. In a very basic configuration 601, computing device 600 typically includes one or more processors 610 and system memory 620. A memory bus 630 may be used for communicating between the processor 610 and the system memory 620.

Depending on the desired configuration, processor 610 may be of any type including but not limited to a microprocessor (µP), a microcontroller (µC), a digital signal processor (DSP), or any combination thereof. Processor 610 may include one more levels of caching, such as a level one cache 611 and a level two cache 612, a processor core 613, and registers 614. An example processor core 613 may include an arithmetic logic unit (ALU), a floating point unit (FPU), a digital signal processing core (DSP Core), or any combination thereof. An example memory controller 615 may also be used with the processor 610, or in some implementations the memory controller 615 may be an internal part of the processor 610.

Depending on the desired configuration, the system memory 620 may be of any type including but not limited to volatile memory (such as RAM), non-volatile memory (such as ROM, flash memory, etc.) or any combination thereof. System memory 620 may include an operating system 621, one or more applications 622, and program data 624. Application 622 may include a fluid flow rate calculation procedure 623 that is arranged to calculate a fluid flow rate of a collected fluid as described herein. Program data 624 may include channel volume, fluid collection area, and/or other information useful for the implementation of the fluid flow rate calculation procedure. In some embodiments, application 622 may be arranged to operate with program data 624 on an operating system 621 such that any of the procedures described herein may be performed. This described basic configuration is illustrated in FIG. 6 by those components within dashed line of the basic configuration 601.

Computing device 600 may have additional features or functionality, and additional interfaces to facilitate communications between the basic configuration 601 and any required devices and interfaces. For example, a bus/interface controller 640 may be used to facilitate communications between the basic configuration 601 and one or more storage devices 750 via a storage interface bus 641. The storage devices 650 may be removable storage devices 751, non-removable storage devices 652, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 620, removable storage 651 and non-removable storage 652 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 642 for facilitating communication from various interface devices (e.g., output interfaces, peripheral interfaces, and communication interfaces) to the basic configuration 601 via the bus/interface controller 640. Example output devices 660 include a graphics processing unit 661 and an audio processing unit 662, which may be configured to communicate to various external devices such as a display or speakers via one or more A/V ports 663. Example peripheral interfaces 670 include a serial interface controller 671 or a parallel interface controller 672, which may be configured to communicate with external devices such as input devices (e.g., keyboard, mouse, pen, voice input device, touch input device, etc.) or other peripheral devices (e.g., printer, scanner, etc.) via one or more I/O ports 673. An example communication device 680 includes a network controller 681, which may be arranged to facilitate communications with one or more other computing devices 690 over a network communication link via one or more communication ports 682.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations.

Figure 7:
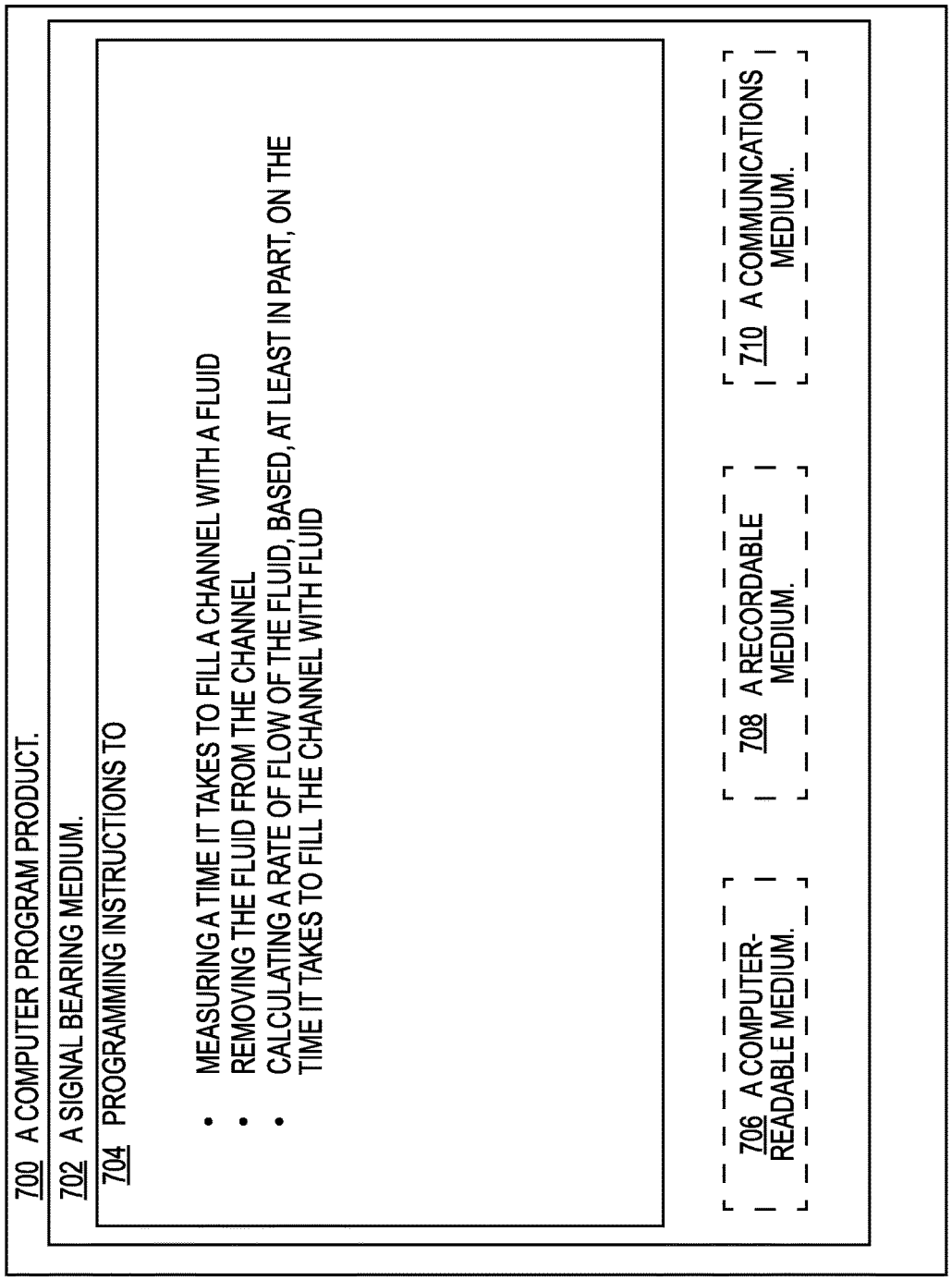
FIG. 7 is a block diagram illustrating an example computer program product that is arranged to store instructions for monitoring a flow rate, all arranged in accordance with at least some embodiments of the present disclosure.

FIG. 7 is a block diagram illustrating an example computer program product 700 that is arranged to store instructions for operating a flow meter and/or calculating a fluid flow rate in accordance with the present disclosure. The signal bearing medium 702 which may be implemented as or include a computer-readable medium 706, a computer recordable medium 708, a computer communications medium 710, or combinations thereof, stores programming instructions 704 that may configure the processing unit to perform all or some of the processes previously described. These instructions may include, for example, one or more executable instructions for measuring a time it takes to fill a channel with a fluid, removing the fluid from the channel, and/or calculating a rate of flow of the fluid, based at least in part, on the time it takes to fill the channel with fluid.

In some embodiments, the computer program product 700 may further store instructions for utilizing data from additional sensors to provide comprehensive real time and cumulative indications of a health status, such as hydration status. Additional data may include hydration status, exercise intensity, movement, heart rate, temperature, and/or sweat composition. Data from other sources may also be utilized by the computer program product in some embodiments, including geolocation, weather, diet, age, gender, and/or weight of a user. In some embodiments, the computer program product 700 may store instructions for providing information on a health status for a given amount of time. In some embodiments, the amount of time is an hour, a day, or a minute. In some embodiments, the computer program product 700 may store instruction for continuously providing information on a health status of a user. In some embodiments, the computer program product 700 may be configured to provide text and/or graphical information to a user on a display coupled to a computing device. In some embodiments, the information may be based, at least in part, on the calculated fluid flow rate and/or additional data.

In some embodiments, a system may include a sensor configured to monitor a flow of a fluid from a bodily surface area through a channel of a volume, a first processor configured to receive signals from the sensor and calculate a flow rate of the fluid, a computing device, including a second processor configured to receive the flow rate of the fluid from the first processor and combine the flow rate of the fluid with additional data to calculate a health status of a user. In some embodiments, the computing device may be implemented using the computing device 600 illustrated in FIG. 6. In some embodiments, the computing device is integrated with the sensor. In some embodiments, the first and/or second processor may be configured to execute at least a portion of a computer product. In some embodiments, the computer product may be implemented as computer program product 700 illustrated in FIG. 7. In some embodiments, the additional data may include at least one of a temperature, an exercise intensity of the user, or a heart rate of the user. In some embodiments, the second processor may be further configured to calculate a perspiration rate of the user based, at least in part, on the flow rate of the fluid. In some embodiments, the health status may be a hydration status of the user. In some embodiments, the computing device may be configured to receive the additional data from additional sensors that may be different from the sensor configured to monitor the flow of the fluid. In some embodiments, the first processor may be wirelessly coupled to the computing device.

In some embodiments, the sensor may be included in an apparatus. In some embodiments, the apparatus may be implemented using flow meter 100 illustrated in FIG. 1. In some embodiments, the apparatus may include a substrate which may have a surface, a channel which may have a volume defined, at least in part, by the substrate, wherein the channel may have a first end and a second end, a valve coupled to the channel at the first end, wherein the valve may be configured to allow a fluid to pass into the channel when the valve is open, and a continuity detector coupled to the channel at the second end, wherein the continuity detector may be activated when the fluid contacts the continuity detector, wherein the continuity detector may be further configured to provide a signal to close the valve and remove the fluid from the channel.

In some embodiments, the substrate may include a piezoelectric material. In some embodiments, the piezoelectric material may be configured to be activated by the signal provided by the continuity detector, wherein activation of the piezoelectric material may close the valve and remove the fluid from the channel. In some embodiments, activation of the piezoelectric material may remove the fluid from the channel at least in part by contracting the channel and ejecting the fluid through an opening at the second end of the channel.

In some embodiments, the apparatus may further include a seal coupled to a perimeter of the surface of the substrate, wherein the seal may be impermeable to fluids. In some embodiments, the seal may include an adhesive material that may be configured to adhere the substrate to another surface.

In some embodiments, the apparatus may include an absorbent material coupled to the surface of the substrate, wherein the absorbent material may include a portion proximate the first end of the channel. In some embodiments, the absorbent material may be saturated with a priming fluid. In some embodiments, the absorbent material may include a branched conduit system configured to draw fluid from another surface in contact with the absorbent material to the valve. In some embodiments, the absorbent material may comprise a sponge or other porous material, a gel (such as a hydrogel), an absorbent woven material, a fabric, an absorbent fibrous material, or an arrangement of capillaries (such as capillaries etched into a polymer or other material). In some examples, a woven or otherwise fibrous or structured material may be formed from an otherwise non-absorbent material, in which voids and channels between the fibers and/or other structures may be used to absorb a volume of water. In some examples, capillaries (such as fluidic channels, fluid conduits, microchannels, microtubes, and the like) may be configured to draw fluid from a skin surface of a subject using capillary forces, and direct the fluid to one or more pump locations, such as one or more piezoelectric pumps. Capillaries may be arranged in a branched arrangement, the branches being configured to draw fluid to one or more pump locations.

In some embodiments, the apparatus may further include a clock coupled to the continuity detector, wherein the clock may be configured to measure a time period and reset when the continuity detector is activated, and a processor coupled to the clock, wherein the processor may be configured to receive the time period from the clock and calculate a rate of flow of the fluid through the channel, based at least in part on the time period from the clock and the volume of the channel. In some embodiments, the processor may be at least a portion of a computing device, for example, computing device 600. In some embodiments, the clock may also be included in the computing device.

In some embodiments, the substrate may include an electromagnetic actuator. In some embodiments, the volume may be a volume between 100 nanoliters and 10 microliters. In some embodiments, the apparatus may further include an electrochemical sensor coupled to the channel at the second end, wherein the electrochemical sensor may be configured to sense a chemical in the fluid.

In some embodiments, an apparatus may be configured as a wearable sensor, for example being supported on a body portion of a living subject using one or more straps, adhesive patches, clips, and the like. In some examples, an apparatus may be combined with other functionality, such as one or more of a wristwatch, cardiac monitor, other medical monitoring device, internet device, communication device, a head-supported apparatus, and the like.

In some examples, described approaches provide an improved method of monitoring the hydration state of a living subject, such as a human (such as an athlete, a medical patient, and the like), or non-human animal. In some examples, improved hydration management of patients with cardiovascular and/or renal complications may be achieved, as well as patients with a fever. In some examples, automatic hydration of a patient may be initiated, for example using an automated saline infusion based on hydration status information, or by providing instructions to the living subject or a caregiver therefor to administer fluid to the living subject.

In some examples, a flow rate sensor as described in examples herein may be used in an improved environmental sensor (for example, in combination with chemical analysis techniques for pollution monitoring, water quality sensing, and the like), microfluidic devices, chemical analytical devices, biochemical analytic devices, and the like.

In some examples, an apparatus may be calibrated to an individual configuration or subject. In some examples, a system may monitor a subject's sweat rate over a time interval, and afterwards compared with another measurement of sweat rate, such as a wash-down method, weight monitoring, or other approach. In some examples, a reference absorbent pad may be placed on a subject's body, and the pad can be weighed before and after an exercise session or other time interval to determine the amount of fluid absorbed by the reference absorbent pad. The fluid amount may be compared to the apparatus measurements, e.g. during the same time interval, from an apparatus located in a similar location, for example, symmetrically positioned about the body. In some examples, an apparatus may be placed on a left part of the body (such as a left arm, leg, or torso), and a reference absorbent pad placed on a similar location on the right part of the body (or vice versa). A reference absorbent pad may be placed adjacent or otherwise proximate an apparatus.

A calibration process may be repeated at intervals to maintain or improve the apparatus accuracy. In some examples, an apparatus calibration may include digital imaging or 3D modeling of the channel to measure the volume of the channel. In some example, calibration may include running the apparatus and collecting and measuring fluid at the exit point using another method, for example using volumetric or mass based measurements of the collected fluid. Determining an average value of the cycle volume, and optionally the variance of the measurements, may be useful in determining the sweat rate and hydration data.

In some examples, a software program, for example executed on a processor of the apparatus or other device in communication with the apparatus, may be used to analyze hydration data. In some examples, hydration data provided by an apparatus may be analyzed along with other data, such as one or more of other data related to hydration status, exercise intensity (e.g. using data provided by an exercise machine, accelerometer mounted on the subject body, and the like), subject movement, speed (e.g. as provided by a speed sensor, global positioning system, and the like), heart rate, ambient temperature, body temperature (such as skin temperature and/or core body temperature), sweat composition, and the like, and may provide real-time indication of subject hydration status. In some examples, a software program may also allow input of other related data (such as a subject's sex, age, weight, species, and other health statistics), ambient data such as weather-related conditions (such as heat, humidity, and the like), geolocation data (including position, altitude, speed, and the like), and/or other information. In some examples, a software program may allow input of consumed items (such as what the person ate and drank, and when), as well as other outputs (such as time and quantity of urination, defecation, vomiting, and the like). A software program may be used to create a model of a subject's total body water turnover, for example for a time interval and/or activity. In some examples, the determined total body water turnover model may be used to determine a hydration status of the subject during a time period without measurements by the apparatus. For example using a sub-set of sensors such as a heart rate sensor and an ambient temperature sensor.

In some examples, an apparatus may include one or more additional sensors, or may in communication with other devices providing data. In some examples, an apparatus may further comprise one or more of an optical sensor (for example sensitive to one or more wavelengths or spectral bands), an IR sensor, and/or an electrochemical sensor (e.g. configured to provide data related to sweat composition such as ion concentration and/or ion composition, lactate concentration, osmolarity of the sweat, and the like). Additional sensors may be used to interrogate the sweat at any point in the apparatus, for example proximate a conductivity sensor, at any flow channel, and the like.

In some examples, a chamber may comprise a rigid polymer (such as HDPE, ABS, and the like), and may comprise a molded polymer and/or 3D printed components. In some examples, a seal may comprise an O-ring that is adhered to the bottom surface. In some examples, an absorbent material of a size and shape appropriate to the sensor can be inserted and optionally adhered to the internal portion of the chamber. In some examples, a hole for the valve may be provided e.g. by molding, drilling, and the like. A piezoelectric material, such as PVDF or inorganic piezoelectric material, may be adhered to or otherwise located at the top surface of the chamber, and electrodes disposed thereon and electrically connected to a control circuit. A lid may be located on top of the channel to create a water-tight seal over the channel using any appropriate configuration.

In some examples, a method, such as a method of determining a sweat rate and/or a hydration state of a living subject, comprises collecting a fluid from a bodily surface of the living subject (such a portion of a skin surface) into a body-worn device, filling a channel of the body-worn device with the fluid, measuring, using the body-worn device, a time it takes to fill the channel with the fluid, removing the fluid from the channel, and calculating, using the body-worn device, a rate of flow of the fluid based, at least in part, on the time it takes to fill the channel with the fluid. In some examples, the fluid comprises sweat. In some examples, the method may further comprise calculating a rate of perspiration of a living subject based, at least in part, on the rate of flow of the fluid, and, in some examples, using a determined area of the bodily surface from which the fluid is collected.

The present disclosure is not to be limited in terms of the particular examples described in this application, which are intended as illustrations of various aspects. Many modifications and examples can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and examples are intended to fall within the scope of the appended claims. The present disclosure includes the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

While the foregoing detailed description has set forth various examples of the devices and/or processes via the use of block diagrams, flowcharts, and/or examples, such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. For example, if a user determines that speed and accuracy are paramount, the user may opt for a mainly hardware and/or firmware vehicle; if flexibility is paramount, the user may opt for a mainly software implementation; or, yet again alternatively, the user may opt for some combination of hardware, software, and/or firmware.

In addition, those skilled in the art will appreciate that the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. An apparatus, comprising:
 a substrate having a surface and a channel, wherein the channel includes a first end, a second end, and a body with a volume;
 a valve coupled to the channel at the first end, wherein the valve is configured to allow a fluid to pass into the channel when the valve is open; and
 a continuity detector electrically coupled to the valve and to the channel at the second end, wherein the continuity detector is configured to be activated when the fluid in the channel fills the volume and contacts the continuity detector, and wherein the continuity detector is further configured to transmit a signal to cause the valve to close and to cause the body of the channel to contract and eject the fluid through the second end of the channel.

2. The apparatus of claim 1, wherein the substrate comprises a piezoelectric material.

3. The apparatus of claim 2, wherein the piezoelectric material is configured to be activated by the signal transmitted by the continuity detector, and wherein activation of the piezoelectric material causes the valve to close and causes the body of the channel to contract and eject the fluid through the second end of the channel.

4. The apparatus of claim 1, further comprising a seal coupled to a perimeter of the surface of the substrate, wherein the seal is impermeable to fluids.

5. The apparatus of claim 4, wherein the seal comprises an adhesive material configured to adhere the substrate to another surface.

6. The apparatus of claim 1, further comprising an absorbent material coupled to the surface of the substrate, wherein the absorbent material includes a portion proximate to the first end of the channel.

7. The apparatus of claim 6, wherein the absorbent material is saturated with a priming fluid.

8. The apparatus of claim 6, wherein the surface includes a first surface, and wherein the absorbent material includes a branched conduit system configured to draw fluid from a second surface in contact with the absorbent material to the valve.

9. The apparatus of claim 1, further comprising:
 a clock coupled to the continuity detector, wherein the clock is configured to measure a time period so as to provide a time period measurement and configured to reset when the continuity detector is activated; and
 a processor coupled to the clock, wherein the processor is configured to receive the time period measurement from the clock and calculate a rate of flow of the fluid through the channel, based at least in part on the time period measurement from the clock and the volume of the body of the channel.

10. The apparatus of claim 9, wherein the rate of flow of the fluid through the channel is calculated based at least in part on a number of activations of the continuity detector.

11. The apparatus of claim 9, wherein the rate of flow of the fluid through the channel is calculated based at least in part on a number of times that the fluid is removed from the channel.

12. The apparatus of claim 1, wherein the substrate comprises an electromagnetic actuator.

13. The apparatus of claim 1, wherein the volume is between 100 nanoliters and 10 microliters.

14. The apparatus of claim 1, further comprising an electrochemical sensor coupled to the channel at the second end, wherein the electrochemical sensor is configured to sense a chemical in the fluid.

15. An apparatus, comprising:
 a substrate having a surface and a channel, wherein the channel includes a first end, a second end, and a body with a volume, and wherein the first end of the channel is configured to allow a fluid to pass into the channel;
 a valve coupled to the channel at the second end, wherein the valve is configured to control passage of the fluid through the channel; and
 a continuity detector electrically coupled to the valve and to the channel at the second end, wherein the continuity detector is configured to be activated when the fluid in the channel fills the volume and contacts the continuity detector, and wherein the continuity detector is further configured to cause the body of the channel to contract and eject the fluid through the valve of the channel.

16. The apparatus of claim 1, wherein the continuity detector is further configured to transmit a signal to cause the first end of the channel to close.

17. The apparatus of claim 1, wherein the continuity detector is further configured to determine at least one of: analytes in the fluid, a temperature of the fluid, and a pH level of the fluid.

* * * * *